US00PP33764P2

(12) United States Plant Patent
Hansen

(10) Patent No.: US PP33,764 P2
(45) Date of Patent: Dec. 21, 2021

(54) ***DIGITALIS* HYBRID PLANT NAMED 'RISING PHOENIX'**

(50) Latin Name: ***Digitalis* x *valanii***
Varietal Denomination: Rising Phoenix

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/300,436

(22) Filed: Jun. 29, 2021

(51) Int. Cl.
*A01H 5/02* (2018.01)
*A01H 6/68* (2018.01)

(52) U.S. Cl.
USPC ..... Plt./263.1
CPC ..... *A01H 6/68* (2018.05)

(58) Field of Classification Search
USPC ..... Plt./263.1
CPC ..... A01H 5/02
See application file for complete search history.

*Primary Examiner* — Kent L Bell

(57) ABSTRACT

The new and distinct cultivar of *Digitalis* interspecific hybrid plant named 'Rising Phoenix' is characterized by sturdy, upright flowering habit with dark-green, serrate foliage and densely-branched flower stems with flowers that are open-faced, campanulate, self-cleaning, non-secund, deep raspberry-pink with light peach interior and long-blooming. The flowers produce an abundance of nectar and are attractive to hummingbirds in the landscape. The new plant is useful in the garden landscape, as a container plant or as a cut flower.

2 Drawing Sheets

Botanical designation: *Digitalis* x *valanii.*
Cultivar denomination: 'Rising Phoenix'.

STATEMENT REGARDING PRIOR DISCLOSURES UNDER 37 CFR 1.77(B)(6)

The first non-enabling disclosures are a posting on Feb. 1, 2021 by Walters Gardens, Inc. on their website and a brief description and photograph in the "Walters Gardens 2021-2022 Catalog" first distributed on May 21, 2021. Information for these plants was obtained from the inventor. No plants of *Digitalis* 'Rising Phoenix' have been sold, in this country or anywhere in the world nor has any disclosure of the new plant been made more than one year prior to the filing date of this application, and such disclosure within one year was obtained either directly or indirectly from the inventor.

BACKGROUND OF THE INVENTION

The present invention relates to a new and distinct cultivar of hybrid plant, botanically known as *Digitalis purpurea* x *Digitalis canariensis*. The new *Digitalis* x *valinii* 'Rising Phoenix' is the product of a planned breeding program conducted by the inventor at a wholesale perennial nursery in Zeeland, Mich., USA. The objective of the breeding program was to create novel interspecific hybrid cultivars between *Digitalis purpurea* and *Digitalis canariensis* with excellent flowers, foliage and habit.

The new interspecific *Digitalis* hybrid was a planned cross between a proprietary, spotted, selection of the seed cultivar *Digitalis purpurea* 'Foxy' (not patented) as the female or seed parent times a proprietary selection of *Digitalis canariensis* (not patented) as the male or pollen parent January of 2012 and later assigned the breeder code of 12-03-02. After further evaluation 'Rising Phoenix' was selected as a single plant from among several hundred crosses between various forms of such *Digitalis* x *valinii* hybrids and first asexually propagated by basal shoot cuttings in the summer of 2013 at the same wholesale perennial nursery in Zeeland, Mich. The new plant has since also been successfully asexually propagated by sterile shoot tip tissue culture. All of the resultant asexually propagated plants by cuttings and tissue culture have remained stable and reproduced true to type in successive generations.

SUMMARY OF THE INVENTION

Plants of the hybrid plant cultivar *Digitalis* x *valinii* 'Rising Phoenix' have not been observed under all possible environmental conditions. The phenotype may vary somewhat with variations in environment such as fertilizer, temperature, light intensity and photoperiod and plant growth regulators without, however, any variance in genotype.

The following traits in combination with one another have been repeatedly observed and are determined to be the unique characteristics of 'Rising Phoenix':

1. Sturdy, upright flowering habit;
2. Moderate number of stiff basal branches extending bloom season from spring until frost;
3. Medium, open-faced, campanulate-formed, horizontal-facing, long-blooming, self-cleaning, non-secund flowers of deep raspberry-pink with light peach insides;
4. Broad, dark-green, sparsely-pubescent, basal and cauline, serrate leaves.

Plants of the new *Digitalis* can be compared to the female parent, *Digitalis purpurea* 'Foxy' has longer, broader fertile flowers of purple, without the light peach inside color, on shorter plants, the petal lobe apices are rounded and the flowering season is shorter. The male parent has dark, glossy, glabrous foliage with shrub-like habit with less branching of the flower stems, and the flowers are deeper reddish-orange in color with a larger lower lip on darker stems. The new plant is also more herbaceous producing more basal rosettes and branches than the male parent which is less branched and more shrub-like.

Other closely comparable plants include, 'Berry Canary' U.S. Plant Pat. No. 27,607, 'Firebird' U.S. Plant Pat. No. 31,840, 'Flame' (not patented), 'Falcon Fire' (not patented) and 'Firecracker' U.S. Plant Pat. No. 32,975. 'Berry Canary' has a shorter habit and larger flowers of hot pink with light yellow throats with burgundy speckling. 'Firebird' has a taller habit, and flowers of coppery-pink with soft orange throats having pinkish purple spotting. 'Flame' has a taller and broader habit with smaller flowers with a more orangish-red in the outside and peachy-orange in the inside with orangish-red spotting. 'Falcon Fire' has a larger habit with flower petals having an outer surface color of deep pink with and the inner surface of mango-orange and dark wine-colored spotting. 'Firecracker' has smaller and narrower flowers that are vivid orange-yellow with a blush of rosy-pink, and the petal lobe apices are all acute.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plants used in the drawings are second-year growing plants following a vernalization period of about 8 weeks, grown in a greenhouse at a wholesale nursery in Zeeland, Mich. with supplemental fertilizer but without plant growth regulators.

DETAILED BOTANICAL DESCRIPTION

Figure 1:
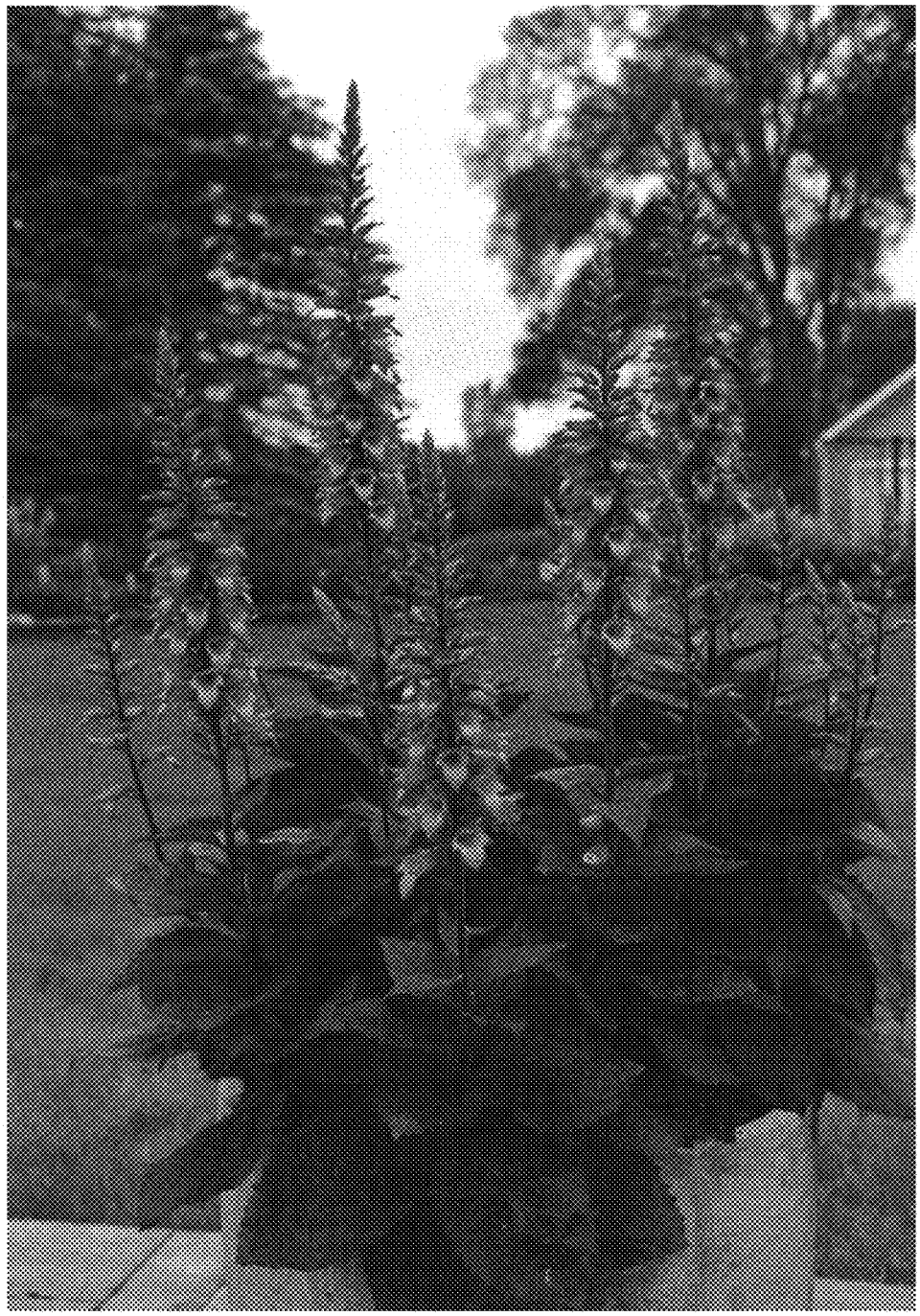
FIG. 1 shows the plant compact, dense, upright, flowering habit of a two-year-old plant.
Figure 2:
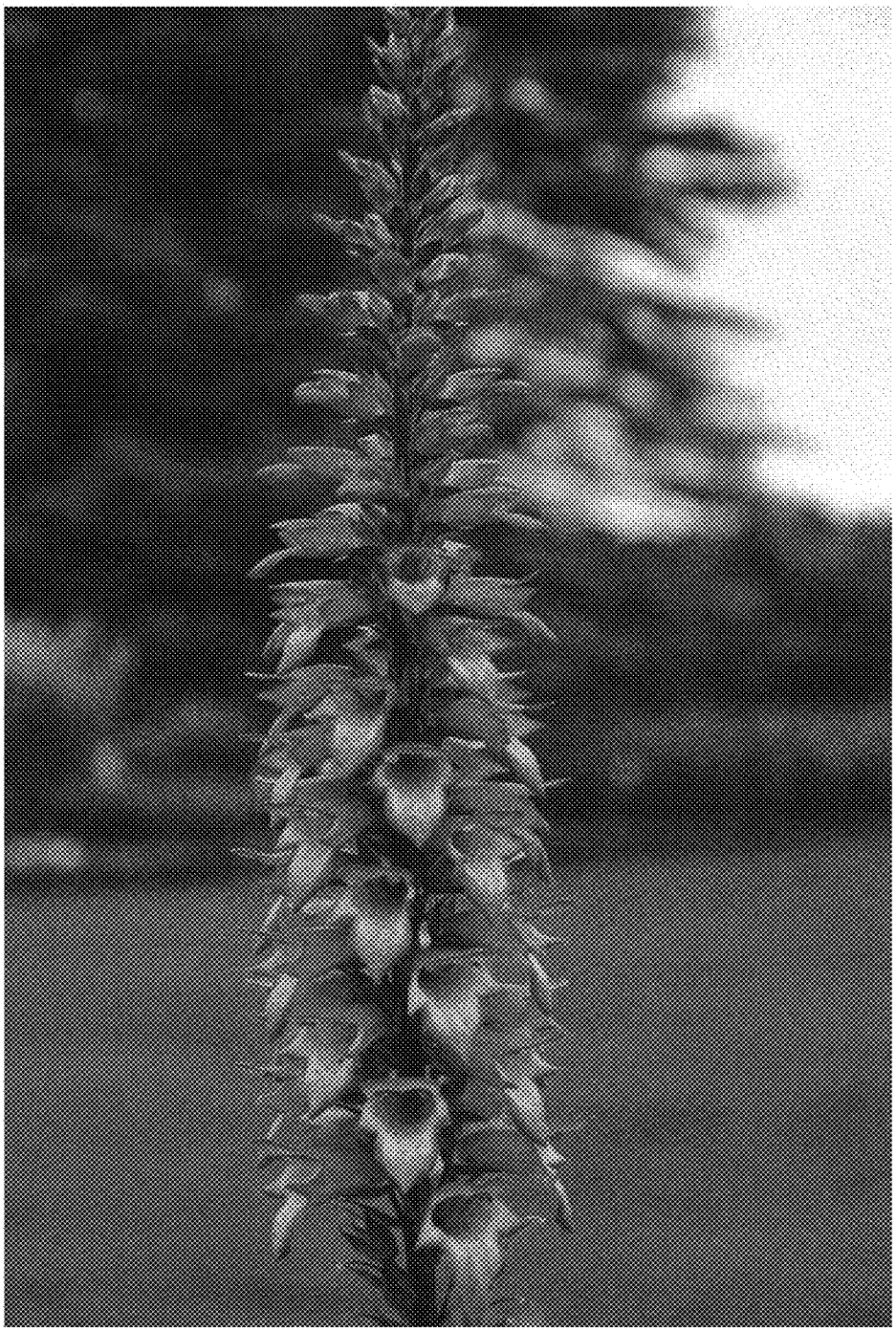
FIG. 2 shows a close-up of the flowers and buds on the scape.

The following descriptions and color references are based on the 2015 edition of The Royal Horticultural Society Colour Chart except where common dictionary terms are used. The new plant, *Digitalis* x *valinii* 'Rising Phoenix', has not been observed under all possible environments. The phenotype may vary slightly with different environmental conditions, such as temperature, light, fertility, moisture and maturity levels, but without any change in the genotype. The following observations and size descriptions are of two-year-old plants in the greenhouses of a nursery in Zeeland, Mich. with supplemental fertilizer and water as needed.

Parentage: Female, or seed parent an unreleased selection of *Digitalis purpurea* 'Foxy'; male, or pollen parent an unnamed, unreleased, proprietary selection of *Digitalis canariensis;*

Propagation method: Shoot tip cuttings and sterile shoot tip plant tissue culture division.

Root description: Fine, freely branching; color creamy-white, nearest RHS 15D;

Time to initiate roots from tissue culture: About two weeks;

Crop time: Under normal cool spring growing conditions of 12° to 15° C., finished flowering plants can be obtained in about 8 to 10 weeks from a vernalized 25 mm plug;

Plant vigor: Very good;

Plant habit: Perennial, winter hardy from at least USDA zone 8 through 10 but capable of growing in colder regions as an annual; upright and dense; leaves basally whorled, cauline dextrorse to alternate and tightly arranged; with branching on nearly every node below individual flowers;

Main stem: Stiff and erect; about 105.0 cm long and 1.8 cm diameter at base; densely and finely puberulent; cylindrical with basal portion having thick ridges extended from central leaf veins; length of ridges extends to next lower leaf directly below; with basal branches and axillary branches;

Main stem color: Variable, nearest RHS 187B proximally and distally with some portions receiving low light exposure between RHS 145A and RHS 146D;

Branch color: Nearest RHS 187B with portions in less intense light exposure with undertones of nearest RHS 146C;

Nodes: About 32 per main stem before unbranched flowers; about 12.0 mm apart in lower stem below individual flower and 4.7 mm apart in upper portion of individual flowers;

Node color: In long light nearest RHS 146D with portions receiving higher light exposure moderately to lightly blushed nearest RHS 178B;

Branches: Outwardly in proximal portion, then upright next to main stem; to about 48 cm long and 9.0 mm diameter; densely puberulent; about 4 main branches per plant from lower nodes and 8 branches in upper nodes below individual flowers; color same as main stem;

Foliage: Basally whorled and ovate; cauline dextrorse to alternate and lanceolate sessile; acute apex and attenuate sessile base; puberulent on abaxial surface and glabrous adaxial; serrate and glabrous margin; slightly lustrous adaxial, slightly lustrous to matte abaxial;

Leaf size: Basal to about 24.0 cm long at base and 14.5 cm wide at widest point near base, cauline to about 23.0 cm long and 14.0 cm wide, decreasing distally; about 16 leaves per main stem below initial flowers;

Leaf blade color: Basal and cauline adaxial nearest RHS NN137A, basal and cauline abaxial nearest RHS 147B;

Veins: Pinnate; puberulent abaxial and sparsely puberulent adaxial; costate on abaxial and slightly impressed adaxial;

Vein color: Adaxial midrib and proximal primary veins nearest RHS 145A, secondary and distal veins nearest RHS NN137A; abaxial midrib and proximal primary veins between RHS 145C and RHS 148C, proximal primary veins nearest RHS 146C, secondary veins and distal primary veins nearest RHS 137B;

Flower: Single; perfect; complete; campanulate; zygomorphic; total corolla average size 44.0 mm long and face opening to 33.0 mm across and 38.0 mm tall, with basal 29.0 mm of corolla tube fused and to about 20.0 mm wide and 17.0 mm tall at fusion; with four main lobes, two side lobes smallest and nearly perpendicular to upper and lower lobes; two side lobes about 9.0 mm wide at fusion and 9.0 mm long from fusion with broadly-acute, slightly reflexed, slightly downwardly pointed apex and micro-ciliolate margin; upper lobe about 20.0 mm wide at fusion and 17.0 mm long beyond fusion, flat, with rounded micro-ciliolate apex; lowest lobe about 17.0 mm wide at fusion and 19.0 mm long beyond fusion, apex typically rounded with slightly revolute and micro-ciliolate; speckling present on adaxial petal surfaces of lower and side lobe surfaces, dorsal and side inner corolla tube adaxial surfaces, on distal abaxial lower lobe in spots between 0.1 mm diameter and 0.7 mm diameter; speckling absent on adaxial and abaxial of upper lobe and abaxial side lobes; sparsely puberulent to glandular on abaxial surfaces and pubescent on adaxial surfaces of middle portion of lower lobe; upper lobe and side lobes glabrous on adaxial surface; not persistent, self-cleaning; produces large amount of nectar;

Flower number: To about 70 per main stem, to about 39 per lateral lower branch and 5 per lateral upper branch;

Flower bud: Oblong flattened tubular; to about 31.0 mm long and 14.0 mm wide near middle and about 8.0 mm tall near apex, constricting in basal 5.0 mm to about 6.0 mm diameter; apex and base rounded;

Flower bud color: Dorsal and side lobes nearest RHS 61A, ventral lobe variable between RHS 71A in distal one-quarter and middle two-thirds of dorsal lobe between RHS 71A and RHS 158A; proximal corolla tube under sepals nearest RHS 158B;

Flower color: Varies with maturity; shortly after opening — ventral abaxial nearest RHS 72A in distal margin, proximally blotchy between RHS NN155B and blend between RHS NN155B and RHS 72A and sparsely spotted with nearest RHS 187C, dorsal abaxial between RHS 71A and RHS 72A, proximal 2.0 mm of corolla tube nearest RHS 145C, and adaxial distally between RHS 72A and RHS 71A along perimeter of each lobe, upper lobe between RHS 11D and RHS 11C, abaxial side and lower lobe nearest RHS 11C with spots of nearest RHS 187B; at pollen dehiscence about five days after opening — abaxial dorsal between RHS 186A and RHS 186B, abaxial ventral proximal margin nearest RHS 158D with moderate to strong blush of nearest RHS 186A and sparse spots of nearest RHS 187B distally, adaxial upper lobe nearest RHS 186A at distal margin and a blend between RHS 23D and RHS 18C in the center portion, side and lower lobes nearest RHS 186A at margin, nearest RHS N172 C just inside margin and central portion between RHS 158A and RHS 168D with spots nearest RHS 187B, basal 5 mm of adaxial and abaxial corolla tube nearest RHS 145D;

Inflorescence: Average size main unbranched stem portion to about 48.0 cm long and 10.0 cm wide;

Flower bract: Lanceolate; sharply acute apex and truncate to rounded sessile base; margin finely serrated proximally and ciliolate proximally and distally; adaxial and abaxial finely puberulent; to about 40.0 mm long and 15.5 mm across near base, decreasing distally;

Flower bract color: Adaxial nearest RHS NN137B, abaxial nearest RHS 147B;

Natural flowering season: Early summer through frost;

Flower longevity: Individual flowers on plant lasting about 7 to 10 days; main flower spike stays in flower for at least three months under ideal conditions;

Fragrance: None detected;

Sepals: Five; persistent; lanceolate; acute apex, truncate base, entire and micro-ciliolate margin; micro-puberulent abaxial and adaxial; about 12.0 mm long and 5.0 mm across at middle, decreasing in distal flowers;

Sepal color: Adaxial nearest RHS 137A, abaxial RHS 137B with portions having high anthocyanin pigmentation to nearest RHS 187A;

Peduncle: Strong, erect; puberulent; to about 54.0 cm long and 10.0 mm in diameter below first flowers;

Peduncle color: Nearest RHS 187B with portions in less intense light exposure with undertones of nearest RHS 146C;

Pedicel: Puberulent; cylindrical; erect to 60 degree angle above horizontal at flower anthesis; to 23.0 mm long and 2.2 mm diameter, decreasing with distal flowers;

Pedicel color: Nearest RHS 146C;

Gynoecium: Single; about 26.0 mm long;

*Style*.—Cylindrical; positioned along adaxial upper lobe; slightly lustrous; about 16.0 mm long and gradually tapering from ovary to stigma to about 0.7 mm diameter; color in young and mature flower center portion nearest RHS 186C, distally toward stigma and proximally toward ovary nearest RHS 185A.

*Stigma*.—Bifid in distal 0.5 mm; to about 1.0 mm long and about 0.5 mm wide; color nearest RHS NN155B.

*Ovary*.—Superior; puberulent to glandular; slightly lustrous; long, conical, apex tapering to meet style, base truncate; about 9.0 mm long and 4.5 mm across at base; color nearest RHS N144D.

Androecium: Four, didynamous; further extending set dehiscing first;

*Filaments*.—Four; cylindrical with basal 7.0 mm portion of both sets flattened and adnate along inside of corolla tube; about 27.0 mm and 31.0 mm long and 1.0 mm across at base; color between RHS 64B and RHS 64A.

*Anther*.—Dorsifixed; folded in middle prior to dehiscence; each half about 4.0 mm long and each half about 1.5 mm across; color prior to dehiscence nearest RHS 12B.

*Pollen*.—Abundant; dust-like; color nearest RHS 11D.

Fruit: Mature seed pods rarely produced;

Seed: Viable seed production has not yet been observed;

Disease and pest resistance or tolerance: 'Rising Phoenix' is not normally bothered by rodents or deer in the landscape. Disease or pest resistance beyond that typical of other *Digitalis* hybrids has not been noted. The new plant performs best in full sun with good drainage and regular watering.

Hardiness: The new plant is winter hardy to approximately USDA zone 8, but requires a vernalization period for best flower production.

It is claimed:

1. A new and distinct cultivar of *Digitalis* hybrid plant named 'Rising Phoenix' as illustrated and described.

* * * * *